(12) United States Patent
Dorn

(10) Patent No.: US 6,251,120 B1
(45) Date of Patent: Jun. 26, 2001

(54) MEDICAL INSTRUMENT FOR REMOVING TISSUE

(75) Inventor: Jürgen Dorn, Neulussheim (DE)

(73) Assignee: Karl Storz GmbH & Co., KG (DE)

( * ) Notice: Subject to any disclaimer, the term of this patent is extended or adjusted under 35 U.S.C. 154(b) by 48 days.

(21) Appl. No.: 09/609,586

(22) Filed: Jun. 30, 2000

Related U.S. Application Data

(63) Continuation of application No. PCT/EP99/08101, filed on Oct. 27, 1999.

(30) Foreign Application Priority Data

Nov. 3, 1998 (DE) .............................................. 198 50 520

(51) Int. Cl.[7] .................................................. A61B 17/32
(52) U.S. Cl. ........................................ 606/170; 606/180
(58) Field of Search ..................................... 606/170, 171, 606/159, 167, 180, 174; 604/22

(56) References Cited

U.S. PATENT DOCUMENTS

| | | | |
|---|---|---|---|
| 5,320,635 | 6/1994 | Smith | 606/180 |
| 5,529,580 | 6/1996 | Kusunoki et al. | 606/170 |
| 5,620,447 | 4/1997 | Smith et al. | 606/79 |
| 5,669,926 | 9/1997 | Aust et al. | 606/170 |
| 5,851,212 * | 12/1998 | Zirps et al. | 606/180 |
| 5,913,867 * | 6/1999 | Dion | 606/170 |

FOREIGN PATENT DOCUMENTS 43 02 912 A1  8/1994 (DE) .
43 23 756 A1  1/1995 (DE) .

* cited by examiner

*Primary Examiner*—Kevin Truong
(74) *Attorney, Agent, or Firm*—St. Onge Steward Johnston & Reens LLC

(57) ABSTRACT

A medical instrument for removing tissue in the human or animal body has a tubular shaft that has at least one window in the region of its distal end. The instrument moreover has a cutting element that is arranged in the shaft in the region of the window and is connected to a drive shaft, extending in the shaft, by way of which the cutting element can be driven rotationally about its longitudinal axis, the shaft having at least one bending point. The drive shaft terminates proximally from the bending point and is connected to the cutting element through the bending point by way of at least one flexible wire element. The wire element is attached to the drive shaft eccentrically with respect to the latter's longitudinal center axis and to the cutting element eccentrically with respect to the latter's longitudinal center axis.

10 Claims, 3 Drawing Sheets

MEDICAL INSTRUMENT FOR REMOVING TISSUE

CROSS-REFERENCE TO PENDING APPLICATION

This is a continuation of pending International Application PCT/EP99/08101 filed Oct. 27, 1999.

BACKGROUND OF THE INVENTION

The present invention relates to a medical instrument for removing tissue in the human or animal body, having a tubular shaft that has at least one window in the region of its distal end, having a cutting element that is arranged in the shaft in the region of the window and is connected to a drive shaft, extending in the shaft, by way of which the cutting element can be driven rotationally about its longitudinal axis, the shaft having at least one bending point, and the drive shaft terminating proximally from the bending point and being connected to the cutting element through the bending point by way of at least one flexible element.

An instrument of this kind is known from U.S. Pat. No. 5,320,635. An instrument of this kind, which is also referred to as a rotary cutting instrument or a shaver, is used in minimally invasive surgery to remove tissue in the human or animal body. For that purpose, the distal end of the shaft is guided through an incision into the surgical area in which the tissue that is to be removed is located. For removal of the tissue, the cutting element is caused to rotate, via the drive shaft, by way of an external or internal motor. A blade configured on the cutting element coacts in cutting fashion, during rotation, with an edge of the window of the shaft also configured as a blade, by the fact that the blades of the cutting element pass by the blades on the window at each revolution.

In addition to instruments that have a continuous straight shaft, instruments of this type are also known whose shaft has a bending point in the region of the distal end, i.e. the shaft is curved in the region of its distal end. Because of the curved configuration of the shaft, it is possible to remove portions of tissue in the body that are inaccessible or difficult to access with a straight shaft. In orthopedics, for example, portions of tissue around joint structures can be removed therewith.

In the case of an instrument having a curved shaft, there arises the problem of transferring the rotation of the inherently rigid drive shaft, through the bending point or curvature of the shaft, to the cutting element; this is problematic because the longitudinal axis and thus the rotation axis of the cutting element, and the longitudinal axis and thus the rotation axis of the drive shaft, enclose an angle that differs from zero.

In the case of the instrument known from the aforementioned U.S. Pat. No. 5,320,635, the rotation transfer through the bending point is brought about in that the drive shaft, configured as a tubular shaft, is equipped, in the region arranged in the bending point, with circumferentially delimited indentations introduced perpendicular to the longitudinal axis in the manner of a bellows, thus making possible flexibility of the drive shaft in this region. Provision is also made for the drive shaft to be made of a flexible plastic at least in this region.

A disadvantage of this configuration, however, is that the slits introduced into the drive shaft can constitute defined break points, since as it rotates, the drive shaft is exposed in the bending region to continuously alternating bending directions. This configuration of the drive shaft, in particular in the case of a miniaturized configuration of the instrument with a thin shaft, is moreover complex in terms of manufacturing and cost, since the slits must be of very fine-scale configuration and suitable tools must be used for the purpose.

A further rotational cutting instrument is known from DE-A-43 23 756. With this instrument, the drive shaft is interrupted in the region of the bending point of the shaft, the respective adjacent ends of the rigid shaft parts being connected via one or more universal joints. The universal joints have two articulation axes orthogonal to one another.

This known type of rotation transfer from the drive shaft to the cutting element again results in a complex design for the instrument. With miniaturized configurations of the instrument in particular, the universal joints must also be of miniaturized configuration. The manufacture of such miniaturized universal joints is, however, laborious.

Also known, from U.S. Pat. No. 5,669,926, is a rotary cutting instrument in which the drive shaft is connected to the cutting element, through a bending point of the tubular shaft, via a flexible coil, the coil having the same diameter as the drive shaft. This type of rotation transfer through a bending point is also associated with increased outlay for manufacture of the drive shaft.

DE 43 02 912 A1 discloses a rotary cutting instrument in which the drive shaft is constructed of gimbal elements in a curvature region of the tubular shaft.

A similar configuration of the drive shaft in the region of a bend in the tubular shaft, by arranging gimbal elements one behind another and in mutual engagement, is known from U.S. Pat. No. 5,755,731.

A drive shaft similar to the configuration of the drive shaft described in the aforementioned U.S. Pat. No. 5,320,635 is known in the case of a rotary cutting instrument disclosed in U.S. Pat. No. 5,620,447.

Lastly, U.S. Pat. No. 5,529,580 discloses a rotary cutting instrument in which the rotation transfer from the drive shaft through a bend in the tubular shaft to the cutting element is accomplished by an element similar to a helical spring.

All the aforementioned known types of flexible configuration of the drive shaft in the region of the bend in the shaft have the disadvantage of being complex in terms of design and production engineering.

It is therefore the object of the invention to develop an instrument of the kind cited initially in such a way that rotation transfer from the drive shaft to the cutting element through the at least one bending point is made possible with little complexity in terms of design.

SUMMARY OF THE INVENTION

According to the present invention this object is achieved by a medical instrument for removing tissue, comprising:

a tubular shaft having a distal end and having at least one window in a region of said distal end, said shaft further having at least one bending point;

a cutting element arranged in said shaft in a region of said window;

a drive shaft extending in said shaft and connected to said cutting element for driving said cutting element rotationally about a longitudinal axis of said cutting element, said drive shaft terminating proximally from said bending point and being connected to said cutting element through said bending point by way of at least one flexible element, wherein said at least one flexible element is configured as a wire element whose diameter is less than a diameter of said drive shaft, and which is attached to at least one of said drive shaft and said cutting element eccentrically with respect to a longitudinal center axis thereof.

Instead of the rotation transfer from the drive shaft to the cutting element provided for in the existing art, by way of a configuration of the drive shaft equipped with indentations or by way of universal joints, in the case of the instrument according to the present invention the rotation transfer is thus brought about by way of at least one flexible wire element that connects the drive shaft to the cutting element. A connection of this kind by way of at least one flexible wire element is very simple in terms of design, so that the instrument according to the present invention can be manufactured economically with little technical complexity. In addition, because of the eccentric attachment of the two wire element ends to the drive shaft on the one hand and to the cutting element on the other hand, a rotation transfer with a favorable torque transfer is achieved. The flexible wire element furthermore has the advantage that it adapts to the curved profile of the bending point of the shaft and is thus suitable for any radius of curvature of the bending point. The wire element can be attached to the drive shaft and to the cutting element at the same angular position in each case, i.e. without a circumferential offset, or at angular positions that are different in terms of the drive shaft and the cutting element.

The provision for attaching the wire element eccentrically with respect to the longitudinal center axis of the drive shaft and eccentrically with respect to the longitudinal center axis of the cutting element furthermore opens up the particularly advantageous possibility of increasing the cutting effect or cutting performance of the instrument according to the present invention, as explained below. This can be achieved, for example if the shaft has only one bending point, by the fact that the wire element is attached to the drive shaft and to the cutting element eccentrically without a circumferential offset. As the wire element rotates about the longitudinal center axis, the cutting element thus executes a rotation about its longitudinal center axis which is superimposed on a slight back-and-forth translational motion. The linear stroke of the translational motion corresponds to the difference between the outer arc length and inner arc length of the inner wall of the shaft in the region of the bending point. As a result of the superimposed rotational and translational motion of the cutting element, the cutting effect of the cutting element as it revolves in the window of the shaft is improved, since the cutting motion has a component not only orthogonal to the blade but also in the longitudinal direction of the blade, so that a pulling cut is made into the tissue. In principle, however, the wire element can be attached to the drive shaft and to the cutting element at any desired angular positions.

The term "wire element" for purposes of the present invention is understood to mean not only a wire made of solid material, but also an elongated hollow body.

The underlying object of the invention is thus completely achieved.

In a preferred embodiment of the invention, the wire element is attached at the circumference of the drive shaft and/or at the circumference of the cutting element.

This embodiment advantageously results in maximal torque transfer from the drive shaft to the cutting element in order to drive the cutting element rotationally. In addition, the aforementioned effect of the translational motion additionally imparted to the cutting element in the direction of its longitudinal center axis can be enhanced by this configuration.

It is preferred in this context if the wire element, in the region of the attachment to the drive shaft and/or in the region of the attachment to the cutting element, is cranked toward the longitudinal center axis of the shaft.

The advantage of this embodiment is that between the drive shaft and the cutting element, the wire element is displaced toward the longitudinal center axis of the shaft, thus reducing friction of the wire element as it revolves in the shaft.

In a further preferred embodiment, the shaft has exactly one bending point, and the wire element is attached to the drive shaft and to the cutting element without circumferential offset.

With this embodiment of the instrument according to the present invention, the back-and-forth translational motion already explained earlier that is imposed on the cutting element in addition to its rotational motion is achieved with a shaft having only one bending point.

In an alternative embodiment, the shaft has two bending points directed oppositely from one another, and the wire element is attached to the drive shaft and to the cutting element without circumferential offset.

This embodiment is advantageous if a translational motion of the cutting element as the cutting element rotates is to be suppressed. If the wire element is attached to the cutting element and to the drive shaft at angular positions identical to one another, the path length differences resulting from the outer arc length and inner arc length of the first bending point, and the outer arc length and inner arc length of the second bending point, almost cancel one another out when the wire element revolves in the shaft. Exact cancellation of these path length differences is accomplished if the radii of curvature of the two bending points are of equal magnitude.

In a further preferred alternative embodiment, the shaft has two bending points directed oppositely from one another, and the wire element is attached to the drive shaft and to the cutting element at angular positions offset approximately 180° from one another.

In an embodiment of the shaft having two bending points that are directed oppositely from one another so that the shaft has an approximately Z-shaped profile, the aforesaid translational motion of the cutting element can be achieved by attaching the wire element with a 180° offset to the drive shaft on the one hand and to the cutting element on the other hand. The translational motion of the cutting element is in fact enhanced with this embodiment, since in this case the path length differences of the outer arc length and inner arc length of the first bending point and the outer arc length and inner arc length of the second bending point are added to one another. The linear stroke of the translational motion can thus be increased further as compared to the linear stroke of the translational motion in the case of the embodiment of the shaft with only one bending point. The embodiment according to the present invention of the instrument is thus particularly suitable even if the shaft has an arbitrary number of bending points, so that a rotational transfer from the drive shaft to the cutting element can be effected regardless of the curved configuration of the shaft.

In a further preferred embodiment, the wire element is a wire made of solid material or a tube whose diameter is less than half the inside diameter of the shaft.

Simple and economical configurations of the at least one wire element are thereby created in a manner that is advantageous in terms of design.

In a further preferred embodiment, the wire element is made of spring steel.

The advantage here is that the wire element has sufficient flexibility to be able to adapt to the profile of the shaft in the region of the bending point. In addition, the wire element achieves sufficient elasticity so that it can withstand over the long term, even at high rotation speeds, the continuously alternating bending stresses that occur as it revolves.

Advantageously, the wire element is attached to the drive shaft and/or to the cutting element by soldering, welding, adhesive bonding, or the like.

These attachment methods are advantageously simple, and further reduce the manufacturing complexity and cost of the instrument according to the present invention.

In a further preferred embodiment, the wire element is inserted with its proximal end into the drive shaft and/or with its distal end into the cutting element.

The advantage here is that insertion of the wire element into the cutting element and/or into the drive shaft results in a connection between the wire element and the cutting element, and/or between the wire element and the drive shaft, that is securely adherent in terms of tangential forces and shear forces.

Further advantages are evident from the description below and from the appended drawings.

It is understood that the features recited above and those yet to be explained below can be used not only in the respective combination indicated, but also in other combinations or in isolation, without leaving the context of the present invention.

BRIEF DESCRIPTION OF THE DRAWING

Exemplary embodiments of the invention are shown in the drawings and will be explained in more detail in the description below. In the drawings.

DETAILED DESCRIPTION OF PREFERRED EMBODIMENTS

Figure 1:
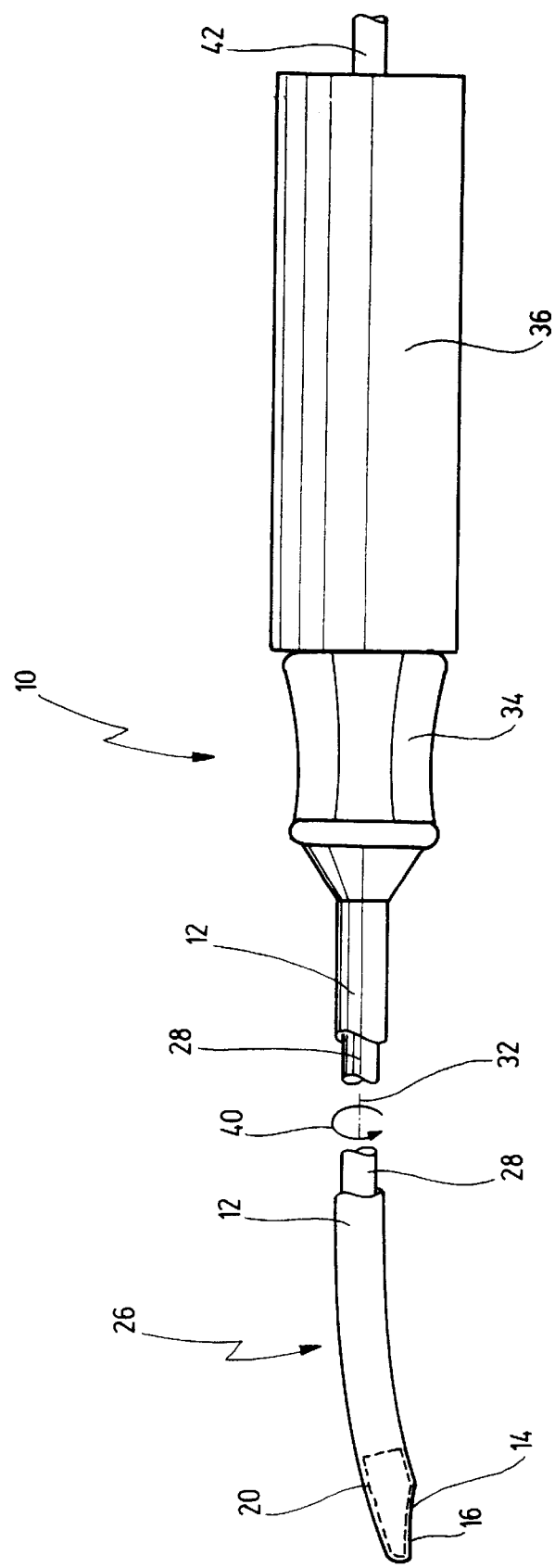
FIG. 1 shows a medical instrument for removing tissue, in a side view.

FIG. 1 shows a medical instrument for removing tissue in the human or animal body, labeled with the general reference character 10. Portions of instrument 10 are further shown in FIGS. 2 through 4.

Instrument 10 has an elongated shaft 12. Shaft 12 is configured as a tube. In the region of its distal end, shaft 12 has a window 14. Window 14 extends over a partial circumferential region of shaft 12. Window 14 constitutes an opening in shaft 12 whose lateral edges 16 (FIG. 1) and 18 (FIG. 4) are configured as cutting edges.

A cutting element 20 is arranged in shaft 12 in the region of window 14. Cutting element 20 is configured in the form of a hollow cylindrical body whose outer contour is adapted to the inner contour of shaft 12, so that cutting element 20 is received conformingly in the distal end of shaft 12.

Cutting element 20 is mounted in shaft 12 rotatably about its longitudinal center axis 22 and against the inner wall of shaft 12. Shaft 12 itself is configured nonrotatably.

Cutting element 20 furthermore has two lateral cutting edges 24 that, as cutting element 20 rotates in shaft 12, pass by edges 16 and 18 of window 14 and can then coact in cutting fashion with them in order to remove tissue. As is evident from FIG. 3, cutting edges 24 can be of toothed configuration.

Shaft 12 furthermore has a bending point 26 at which shaft 12 has a curvature. Cutting element 20 is arranged distally from bending point 26 in a straight segment of shaft 12.

In order to cause cutting element 20 to rotate in order to remove tissue, cutting element 20 is connected to a drive shaft 28. Drive shaft 28 is, like shaft 12, round in cross section. In the exemplary embodiment shown, drive shaft 28 is configured as a hollow cylindrical tube. Drive shaft 28 can also, however, be configured as a solid rod.

A distal end 30 of drive shaft 28 terminates on the proximal side of bending point 26 of shaft 12.

Drive shaft 28 is also of rigid configuration. Drive shaft 28 is received in stationary shaft 12 rotatably about its longitudinal center axis 32.

Shaft 12 is moreover connected nonrotatably, via a coupling 34, to a handle housing 36 that is shown only in FIG. 1.

At the proximal end of drive shaft 28, a further coupling 38, that is also arranged in handle housing 36 in FIG. 1, is connected nonrotatably to it.

Also arranged in handle housing 36 is a drive motor (not shown) to which drive shaft 28 is connected in order to drive the latter rotationally as shown by an arrow 40 in FIG. 1. The motor is impinged upon by current from an external voltage source via a current lead-in cable 42 at the proximal end of handle housing 36.

Figure 2:
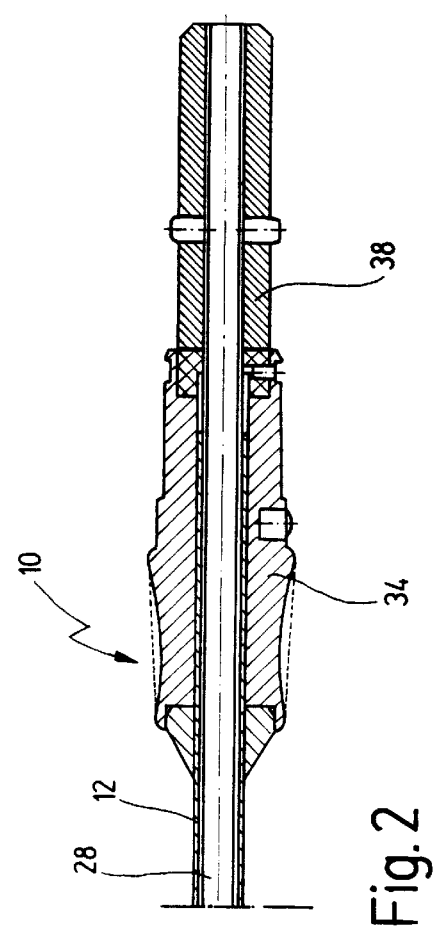
FIG. 2 shows a longitudinal section through the instrument in FIG. 1 with the handle removed.

As is evident from FIG. 2, longitudinal center axis 22 of cutting element 20 and longitudinal center axis 32 of drive shaft 28 form an angle with one another because of bending point 26 of shaft 12. In order to allow the rotation of drive shaft 28 to be transferred to cutting element 20, cutting element 20 is connected to drive shaft 28, through bending point 26, by way of at least one flexible wire element 44.

Wire element 44 is attached at its proximal end 46 to distal end 30 of drive shaft 28, eccentrically with respect to the latter's longitudinal center axis 32.

A distal end 48 of wire element 44 is attached to a proximal end 50 of cutting element 20, also eccentrically with respect to the latter's longitudinal center axis 22. More precisely, proximal end 46, like distal end 48 of wire element 44, is attached to the circumference of drive shaft 28 and to the circumference of cutting element 20 with the maximum possible eccentricity.

Figure 3:
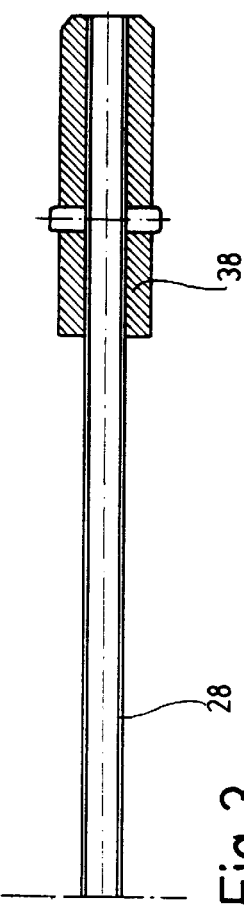
FIG. 3 shows a longitudinal section through the arrangement made up of the drive shaft, wire element, and cutting element in isolation.
Figure 4:
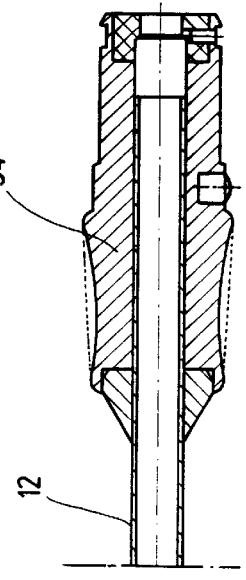
FIG. 4 shows a longitudinal section through the shaft of the instrument in FIG. 1 in isolation.

It is also evident from FIGS. 2 and 3 that wire element 44 is attached to drive shaft 28 and to cutting element 20 without circumferential offset between the two attachment points.

In a region 52 of the attachment of wire element 44 to drive shaft 28, and in a region 54 of the attachment of wire element 44 to cutting element 20, wire element 44 is cranked toward the longitudinal center axis of shaft 12. Wire element 44 is thereby prevented from rubbing against shaft 12 as wire element 44 rotates in shaft 12. The extent of the cranking in regions 52 and 54, as shown in FIG. 2, is such that wire element 44 in shaft 12 still runs outside the longitudinal center axis of shaft 12.

The extent of the cranking in regions 52 and 54 can, however, also be such that wire element 44 essentially lies on the curved longitudinal center axis of shaft 12 in the region of bending point 26.

Wire element 44 is configured as a wire made of solid material or as a thin, flexible tube. If wire element 44 is embodied as a tube, the diameter of the tube is then less than half the inside diameter of shaft 12.

Wire element 44 is preferably fabricated from spring steel.

As is evident from FIG. 3, which shows in isolation the arrangement made up of drive shaft 28, wire element 44, and cutting element 20, wire element 44 assumes a straight-line shape when no bending forces are acting on it. Because of this flexible and (when wire element 44 is at rest) straight configuration of wire element 44, it is capable of adapting to any desired curvature of bending point 26, and even to multiple bends in shaft 12.

The attachment of wire element 44 to drive shaft 28 and to cutting element 20 can be brought about by welding, soldering, adhesive bonding, or the like. Wire element 44 can moreover be inserted into drive shaft 28 and/or into cutting element 20, for which purpose distal end 30 of drive shaft 28, and/or proximal end 50 of cutting element 20, has a longitudinally extending slot into which proximal end 46 and/or distal end 48 of wire element 44 can be inserted.

By way of wire element 44, a rotation of drive shaft 28 as indicated by arrow 40 in FIG. 1 is transferred into a corresponding rotation of cutting element 20 as indicated by an arrow 56 in FIG. 2. The rotation transfer by wire element 44 is accomplished eccentrically with respect to the longitudinal center axis of shaft 12.

Because of this eccentric rotation transfer, the following effect additionally occurs: When wire element 44 is in the rotational position shown in FIG. 2, it lies, in the region of bending point 26, opposite that wall segment of shaft 12 that has an outer arc length $b_a$. As wire element 44 rotates further through 180°, wire element 44 lies opposite that wall segment of shaft 12 that has an inner arc length $b_i$. Since outer arc length $b_a$ is greater than inner arc length $b_i$, but the length of wire element 44 is unchangeable, the result is that during rotation, the eccentric arrangement of wire element 44 causes a back-and-forth displacement of cutting element 20 in the direction of its longitudinal axis 22, as indicated by a double arrow 58.

Cutting element 20 thus executes a rotary motion that is overlain by a translational motion. The linear stroke of the translational motion corresponds to the difference between outer arc length $b_a$ and inner arc length $b_i$. Since this difference is small, the translational motion of cutting element 20 can also be referred to as "microtranslation." The superimposition of rotary motion and oscillating translational motion results in enhanced cutting efficiency for cutting element 20.

Figure 5:
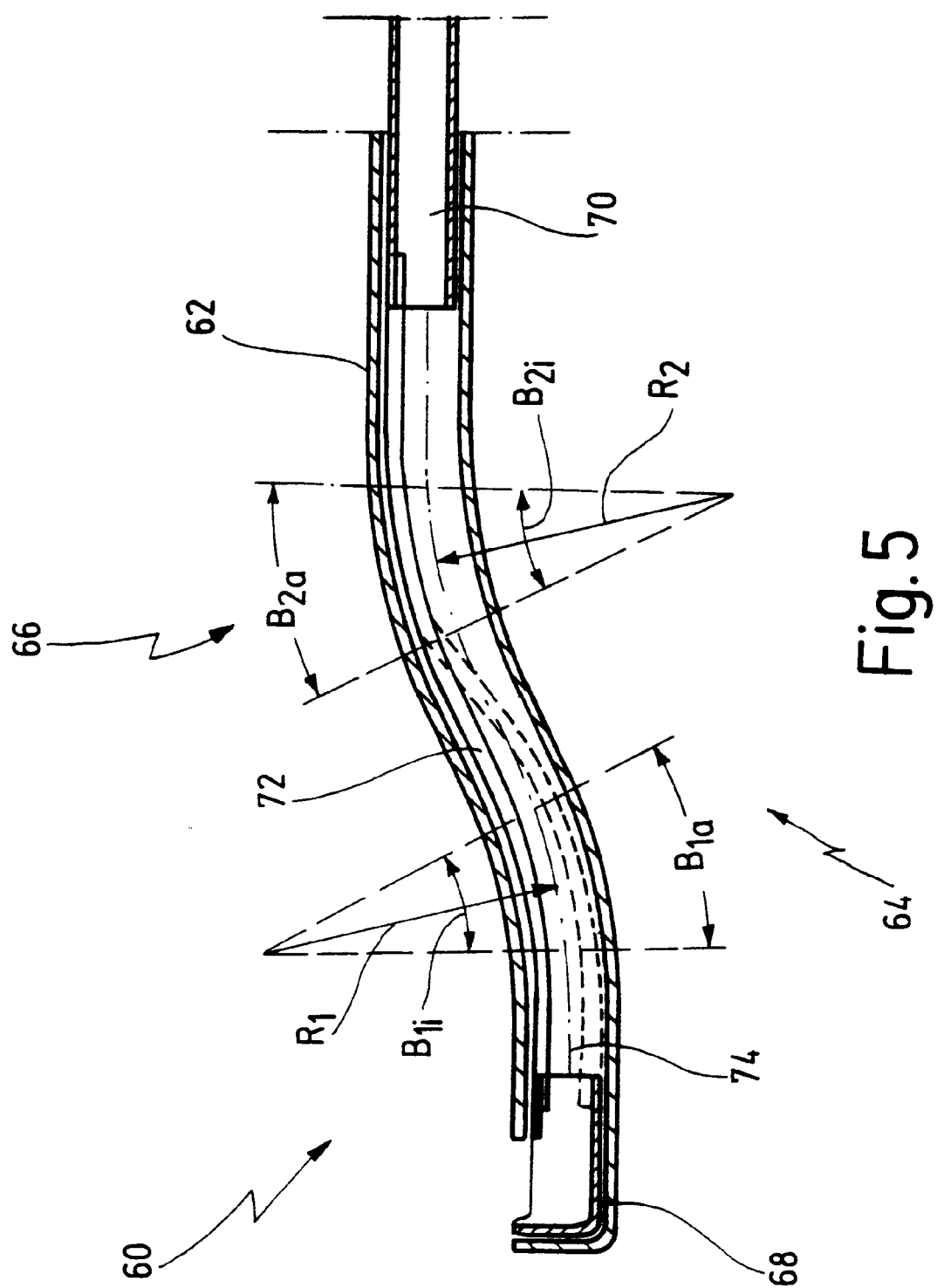
FIG. 5 shows a longitudinal section through the distal region of an instrument for removing tissue, in accordance with a further exemplary embodiment.

FIG. 5 shows a further exemplary embodiment of an instrument given the general reference character 60, instrument 60 being shown only in the region of its distal end.

A shaft 62 of instrument 60 has two bending points, specifically a first bending point 64 and a second bending point 66. First bending point 64 and second bending point 66 are directed oppositely to one another.

A cutting element 68 is connected to a drive shaft 70 via a wire element 72. As in the case of the previous exemplary embodiment, wire element 72 is connected to drive shaft 70 and to cutting element 68 without a circumferential offset.

If a radius of curvature $R_1$ of a longitudinal center axis 74 of shaft 62 at first bending point 64 and a radius of curvature $R_2$ of longitudinal center axis 74 of shaft 62 in the region of second bending point 66 are of equal magnitude, with this arrangement of wire element 72, the translational motion of cutting element 68 upon rotation in shaft 62, as previously described with reference to cutting element 20, is suppressed.

The reason is that in this instance, with identical radii of curvature $R_1$ and $R_2$, the path length differences resulting from an outer arc length $B_{1a}$ and an inner arc length $B_{1i}$ at first bending point 64, and the path length difference resulting from an outer arc length $B_{2a}$ and an inner arc length $B_{2i}$ at second bending point 66, yield an overall compensation to zero, since as it rotates, wire element 72 either lies (at first bending point 64) opposite a wall segment of shaft 62 having the smaller inner arc length $B_{1i}$ and (at second bending point 66) opposite a wall segment of shaft 62 having the longer outer arc length $B_{2a}$, or vice versa if the rotational position is rotated 180°.

When shaft 62 is configured with a double bend as shown in FIG. 5, it is nevertheless also possible to achieve a translational motion of cutting element 68 as it rotates in shaft 62 if wire element 72 is attached to drive shaft 70 and to cutting element 68 in angular positions offset approximately 180°, as shown alternatively with dashed lines. In this case the aforementioned path length differences $(B_{1a}-B_{1i})$ and $(B_{2a}-B_{2i})$ do not compensate for one another, but on the contrary are added to one another. The linear stroke of the translational motion of cutting element 66 can thus in fact be increased as compared to the exemplary embodiment shown in FIGS. 1 through 4 in which shaft 12 has only one bending point.

In the exemplary embodiment shown in FIGS. 1 through 4, provision can also be made to attach wire element 44 to cutting element 20 and to drive shaft 32 at a 180° offset. Wire element 44 and wire element 72 can also be attached, to the drive shaft on the one hand and to the cutting element on the other hand, at attachment points offset in any desired manner. Whereas only one wire element is shown in the Figures, it is also possible in the context of the invention to use two or more wire elements for rotation transfer.

What is claimed is:

1. A medical instrument for removing tissue in the human or animal body, comprising:

a tubular shaft having a distal end and having at least one window in a region of said distal end, said shaft further having at least one bending point;

a cutting element arranged in said shaft in a region of said window;

a drive shaft extending in said shaft and connected to said cutting element for driving said cutting element rotationally about a longitudinal axis of said cutting element, said drive shaft terminating proximally from said bending point and being connected to said cutting element through said bending point by way of at least one flexible element, wherein said at least one flexible element is configured as a wire element whose diameter is less than a diameter of said drive shaft, and which is attached to at least one of said drive shaft and said cutting element eccentrically with respect to a longitudinal center axis thereof.

2. The instrument of claim 1, wherein said wire element is attached at at least one of a circumference of said drive shaft and a circumference of said cutting element.

3. The instrument of claim 2, wherein said wire element is cranked toward a longitudinal center axis of said shaft in at least one of the region of said attachment to the drive shaft and in said region of said attachment to said cutting element.

4. The instrument of claim 1, wherein said shaft has exactly one bending point, and said wire element is attached to said drive shaft and to said cutting element without circumferential offset.

5. The instrument of claim 1, wherein said shaft has two bending points in opposite direction from one another, and said wire element is attached to said drive shaft and to said cutting element without circumferential offset.

6. The instrument of claim 1, wherein said shaft has two bending points in opposite direction from one another, and said wire element is attached to said drive shaft and to said cutting element at angular positions offset approximately 180° from one another.

7. The instrument of claim 1, wherein said wire element is a wire made of solid material or a tube whose diameter is less than half an inside diameter of said shaft.

8. The instrument of claim 1, wherein said wire element is made of spring steel.

9. The instrument of claim 1, wherein said wire element is attached to said drive shaft or to said cutting element by soldering, welding, adhesive bonding, or said like.

10. The instrument of claim 1, wherein said wire element is inserted with its proximal end into said drive shaft or with its distal end into said cutting element.

* * * * *